United States Patent [19]

Spofford et al.

[11] Patent Number: 5,181,509

[45] Date of Patent: * Jan. 26, 1993

[54] TRANSTRACHEAL CATHETER SYSTEM

[76] Inventors: Bryan T. Spofford, 1470 S. Quebec Way, #227; Kent L. Christopher, 9086 E. Colorado Cir., both of Denver, Colo. 80231

[ * ] Notice: The portion of the term of this patent subsequent to Feb. 25, 2009 has been disclaimed.

[21] Appl. No.: 784,123

[22] Filed: Oct. 29, 1991

Related U.S. Application Data

[63] Continuation of Ser. No. 883,409, filed as PCT/US85/02282 on Nov. 19, 1985, abandoned.

[51] Int. Cl.⁵ ............................................ A61M 16/00
[52] U.S. Cl. ........................ 128/207.140; 128/207.170
[58] Field of Search ... 128/200.026, 207.014–207.017, 128/DIG. 26; 604/117, 158, 272, 282, 283, 22, 264, 765

[56] References Cited

U.S. PATENT DOCUMENTS

| 3,688,774 | 9/1972 | Akiyama | 128/200.26 |
| 3,788,326 | 1/1974 | Jacobs | 128/207.15 |
| 3,874,377 | 4/1975 | Davidson | 128/207.15 X |
| 3,880,168 | 4/1975 | Berman | 128/207.15 |
| 4,449,523 | 5/1984 | Szachowicz et al. | 128/200.26 |
| 4,502,482 | 5/1985 | Deluccia et al. | 128/207.15 |
| 4,589,873 | 5/1986 | Schwartz et al. | 604/265 |
| 4,612,927 | 9/1986 | Kruger | 128/200.26 |
| 4,669,463 | 6/1987 | McConnell | 128/207.14 |
| 4,693,243 | 9/1987 | Buras | 128/207.15 |

FOREIGN PATENT DOCUMENTS

| 0131659 | 1/1985 | European Pat. Off. . |
| 2137506 | 10/1984 | United Kingdom . |
| 2171017 | 8/1986 | United Kingdom | 128/207.15 |

Primary Examiner—Kyle L. Howell
Assistant Examiner—John P. Lacyk
Attorney, Agent, or Firm—Dorr, Carson, Sloan & Peterson

[57] ABSTRACT

Apparatus including a series of kits containing apparatus for use in the placement of specific transtracheal catheters for varying periods, including a transtracheal catheter suitable for in-dwelling long-term oxygen supplementation therapy for patients with chronic obstructive pulmonary disease, by its size, perforation location and cleanability, and a method for placement.

21 Claims, 7 Drawing Sheets

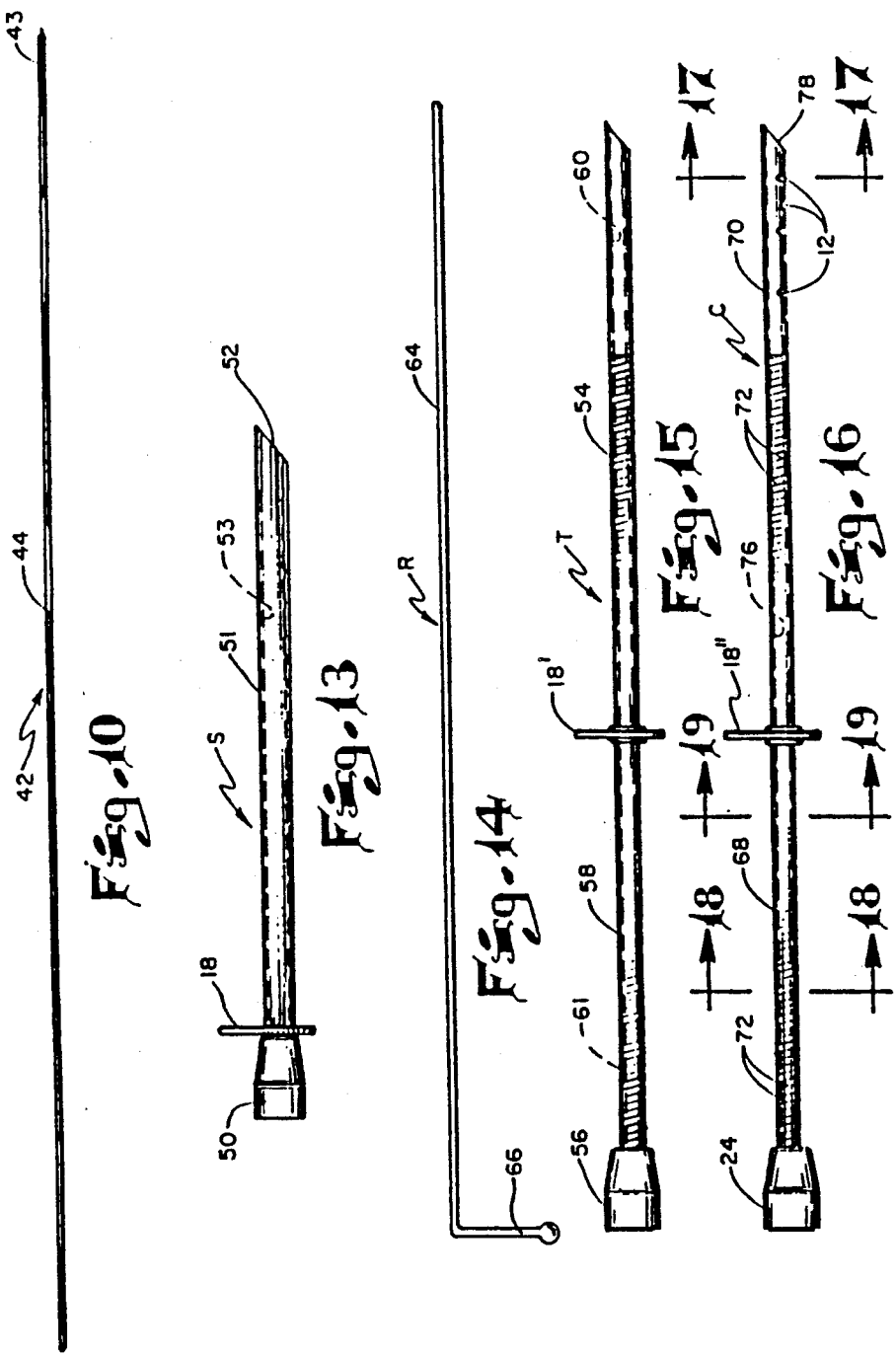

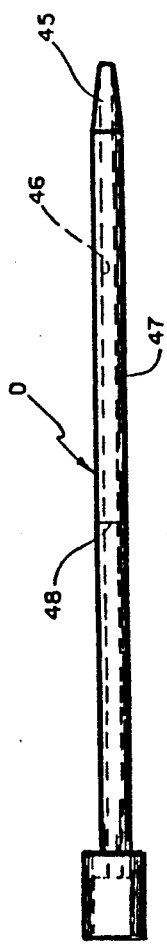
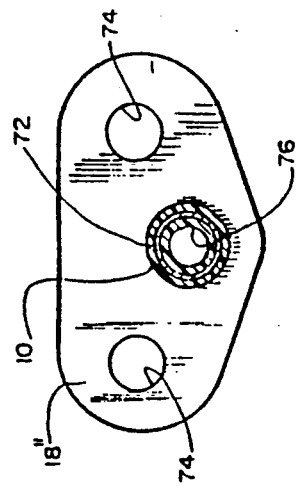
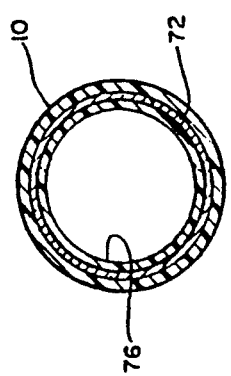
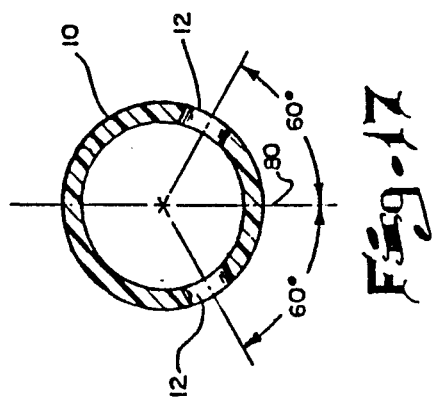

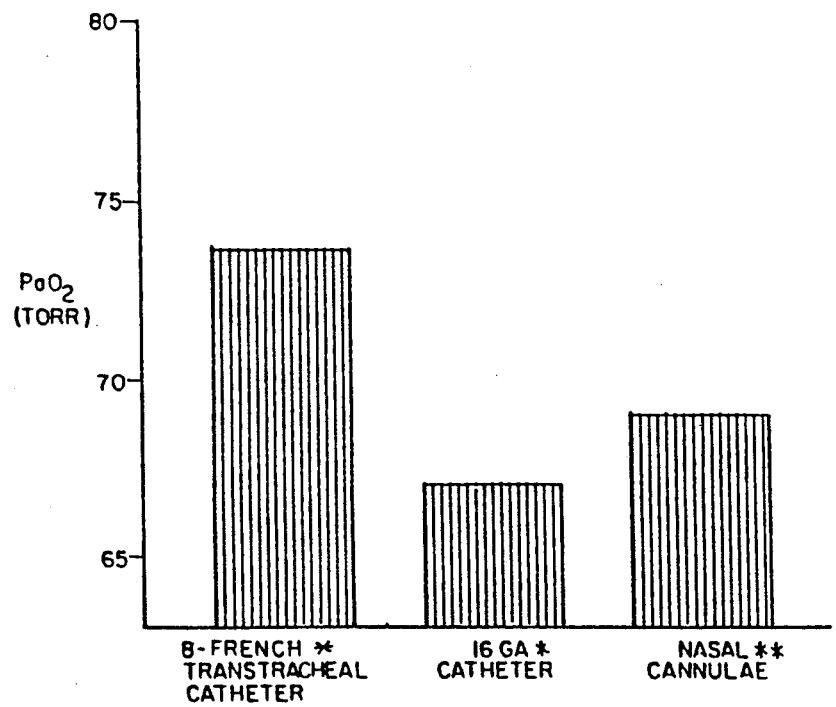
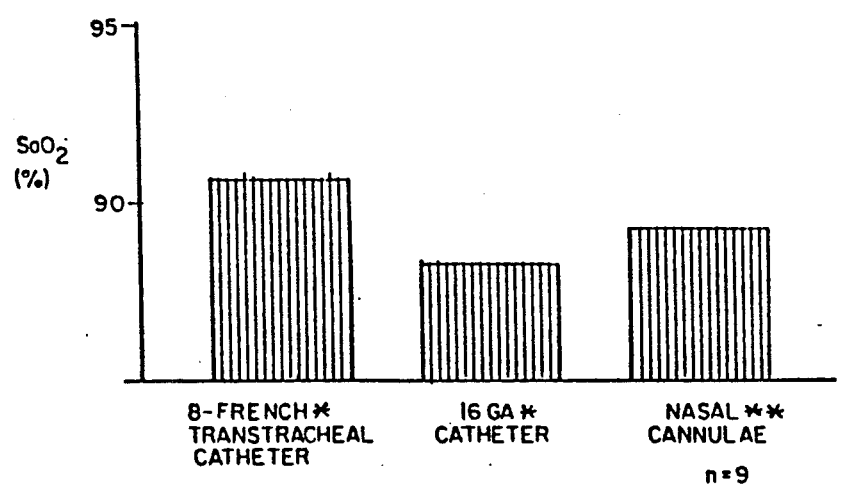
* FLOW = 5.8 L/min.   MAXIMAL EXERCISE
** FLOW = 6.7 L/min.  ARTERIAL BLOOD GASES
Fig-20

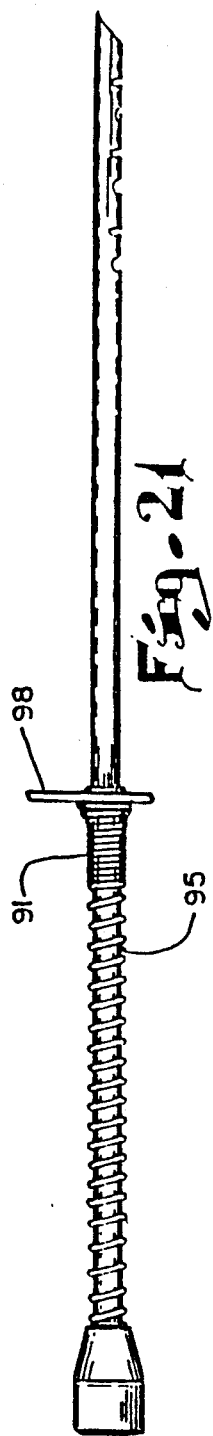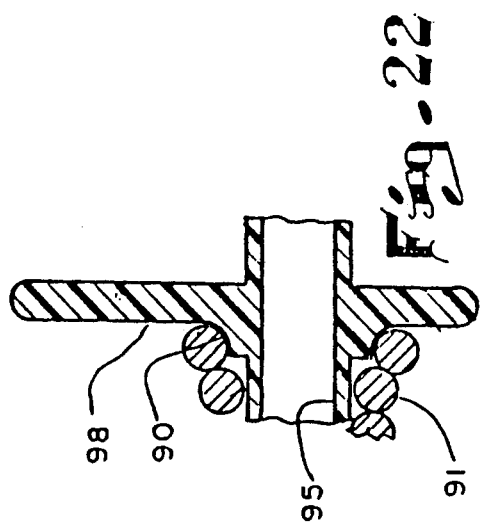

TRANSTRACHEAL CATHETER SYSTEM

This is a continuation of copending application Ser. No. 06/883,409, filed as PCT/US85/02282 on Nov. 19, 1985, now abandoned.

BACKGROUND OF THE INVENTION

TECHNICAL FIELD

This invention pertains to a system for supplemental transtracheal oxygen therapy including transtracheal catheter devices for providing transtracheal oxygen to spontaneously breathing patients with chronic lung disease and to methods for catheter placement and use. Such devices are medically desirable therapy for patients having a chronic need for oxygen where a catheter can be installed on a semi-permanent out patient basis.

As a result of studies that date back to the 1930's and particularly studies conducted in the 1960's and early 1970's, it has been determined that long-term continuous oxygen therapy is beneficial in the treatment of hypoxemic patients with chronic obstructive pulmonary disease (COPD). In other words, a patient's quality and length of life can be improved by providing a constant supplemental supply of oxygen to the patient's lungs.

However, with the current desire to contain medical costs, there is a growing concern that the additional cost of providing continuous oxygen therapy for chronic lung disease will create an excessive increase in the cost of oxygen therapy. Thus, it now desirable that oxygen therapy, when provided, be as cost effective as possible.

The standard treatment for patients requiring supplemental oxygen is still to deliver oxygen from an oxygen source by means of a nasal cannula. Such treatment, however, requires a large amount of oxygen, which is wasteful and can cause soreness and irritation to the nose, as well as being potentially aggravating. Other undesirable effects have also been reported. Other medical approaches which have been proposed to help reduce the cost of continuous oxygen therapy have been studied.

Various devices and methods have been devised for performing emergency cricothyroidotomies and for providing a tracheotomy tube so that a patient whose airway is otherwise blocked may continue to breathe. Such devices, are generally intended only for use with a patient who is not breathing spontaneously and are not intended for the long-term oxygen supplementation therapy for chronic lung disease. Typically, such devices are installed by puncturing the skin to create a hole through the cricoid thyroid membrane above the trachea through which a relatively large curved tracheotomy tube is inserted. As previously described, the use of such tubes has been restricted medically to emergency situations where the patient would otherwise suffocate due to the blockage of the airway. Such emergency tracheotomy tubes are not intended for long-term oxygen supplementation therapy after the airway blockage is removed.

Other devices which have been found satisfactory for emergency or ventilator airway control are described in U.S. Pat. No. 953,922 to Rogers; U.S. Pat. No. 2,873,742 to Shelden; U.S. Pat. No. 3,384,087 to Brummelkamp; U.S. Pat. No. 3,511,243 to Toy; U.S. Pat. No. 3,556,103 to Calhoun; U.S. Pat. No. 2,991,787 to Shelden, et al; U.S. Pat. No. 3,688,773 to Weiss; U.S. Pat. No. 3,817,250 to Weiss, et al.; and U.S. Pat. No. 3,916,903 to Pozzi.

Although tracheotomy tubes are satisfactory for their intended purpose, they are not intended for chronic usage by outpatients as a means for delivering supplemental oxygen to spontaneously breathing patients with COPD. Such tracheotomy tubes are generally designed so as to provide the total air supply to the patient for a relatively short period of time. The tracheotomy tubes are generally of rigid or semi-rigid construction and of large caliber ranging from 2.5 mm outside diameter in infants to 15 mm outside diameter in adults. They are normally inserted in an operating room as a surgical procedure or in the emergency room during emergency situations, through the cricothyroid membrane where the tissue is less vascular and the possibility of bleeding is reduced. These devices are intended to permit passage of air in both directions until normal breathing has been restored by other means.

Another type of tracheotomy tube is disclosed in Jacobs, U.S. Pat. No 3,682,166 and U.S. Pat. No. 3,788,,326. The catheter described therein is placed over 14 or 16 gauge needle and inserted through the cricothyroid membrane for supplying air or oxygen and vacuum on an emergency basis to restore the breathing of a non-breathing patient. Because of resistance to gas flow created by the small inside diameter of the tube, the air or oxygen is supplied at very high pressures, i.e. from 30 to 100 psi for inflation and deflation of the patient's lungs. The Jacobs catheter, like the other tracheotomy tubes previously used, is not intended for long-term outpatient use, and could not easily be adapted to such use.

Due to the limited functionality of tracheotomy tubes, transtracheal catheters have been proposed and used for long-term supplemental oxygen therapy. For example the small diameter transtracheal catheter (16 gauge) developed by Dr. Henry J. Heimlich (described in THE ANNALS OF OTOLOGY, RHINOLOGY & LARYNGOLOGY, Nov.–Dec. 1982; Respiratory Rehabilitation with Transtracheal Oxygen System) has been used by the insertion of a relatively large cutting needle (14 gauge) into the trachea at the mid-point between the cricothyroid membrane and the sternal notch. This catheter size can supply oxygen up to about 2 to 3 liters per minute at low pressures, such as 2 psi, however this flow rate may be insufficient for patients who have higher oxygen requirements. It does not, however, lend itself to convenient outpatient use and maintenance, such as periodic removal and cleaning, primarily because the connector between the catheter and the oxygen supply hose is adjacent and against the anterior portion of the trachea and cannot be easily seen and manipulated by the patient. Furthermore, the catheter is not provided with positive means to protect against kinking or collapsing which would prevent its effective use on an out patient basis. Such a feature is not only desirable but necessary for long-term, out patient and home care use. Also, because of its structure, i.e. only one exit opening, the oxygen from the catheter is directed straight down the trachea toward the bifrucation between the bronchi. Because of the normal anatomy of the bronchi wherein the left bronchus is at a more acute angle to the trachea than the right bronchus, more of the oxygen from that catheter tends to be directed into the right bronchus rather than being directed or mixed for more equal utilization by both bronchi. Also, as structured, the oxygen can strike the mucous membrane of the carina, resulting in an undesirable sensation and a tendency to cough. In addition, in such devices, if a substantial portion of the oxygen is directed against the back wall of the trachea it may result in erosion of the mucosa in this area, this is also undesirable. Overall, because of the limited output from the device, it may not operate to supply sufficient oxygen during supplemental oxygen therapy when the patient is exercising or otherwise quite active or has severe disease.

Thus, none of the prior art devices are fully suitable for outpatient use on a long-term basis.

It is therefore an objective of the present invention to provide a catheter, catheter insertion system and method for catheter insertion and use which will provide for efficient long-term oxygen therapy, particularly for active patients and severely ill patients with high oxygen requirements at rest.

DISCLOSURE OF THE INVENTION

The present invention provides an apparatus for supplying supplemental oxygen to a patient from a portable supply of oxygen which is capable of being carried by such patient, and which oxygen is capable of being introduced uniformly into both of the lungs of such patient on a continuous long-term daily basis by conduction of supplemental oxygen into the cervical trachea (below the cricoid and above the sternal notch) through a catheter disposed in the trachea in a downwardly extending position in the trachea with a distal end portion of such catheter, structured and located in the lower trachea to promote adequate mixing of the oxygen introduced with the air from a normally breathing patient, the catheter apparatus comprising an elongated flexible tube means having a durometer of from about 80 to about 90 Shore A and a length sufficient to locate the distal end portion inwardly within the trachea of the person above the carina; and to locate a proximate end portion outwardly of the neck for attachment of the proximate end portion to a tube connected to a portable supply of oxygen carried by the person; the tube means of said catheter having a lumen having a continuous smooth cylindrical outer peripheral surface and a continuous smooth constant diameter inner peripheral surface defining an elongated continuous cylindrical passage of constant diameter and being made of a flexible grade material having an inside diameter of between 1.7 and 2.5 millimeters; oxygen outlet opening means at the distal end portion of the tubular means including a downwardly and generally anteriorly facing end opening of the same diameter as said continuous oxygen passage means when said tube means is in place in the trachea, and said distal end portion of said tube means additionally containing a plurality of openings located in predetermined spaced relationship above said end opening and extending through said sidewall and facing generally forwardly toward the center of the tracheal air column for supplying oxygen only in a forwardly facing direction whereby rearward flow of oxygen toward the posterior portion of the trachea is limited to prevent erosion of the mucous membranes, said tube means additionally containing reinforcement means mounted either completely within said sidewall between said outer peripheral surface and said inner peripheral surface, or externally of the tube for maintaining a constant lumen cross-section in said tube means by resisting restriction of said central passage means in preselected locations in order to maintain said continuous constant diameter of said central passage means during oxygen therapy use; said tube means also preferably being provided with hydrophilic coating means on the portion which resides inside the trachea and covering the cylindrical outer surface, and the cylindrical inner surface and the side and end opening surfaces for limiting adhesion and subsequent build-up of mucous-type materials present in the trachea which would otherwise restrict the flow of oxygen through said tube means.

In addition, the present invention includes a kit for installing a transtracheal catheter for use in supplying oxygen on a substantially, low pressure basis directly to the bronchi of a spontaneously breathing outpatient for long-term treatment of chronic obstruction pulmonary disease. In a preferred form, the catheter, as previously described, comprises a thin, flexible, kink and collapse resistant, tracheal tube having a proximate end and a distal end. Preferably, reinforcement means such as a coil of wire or other reinforcing material is molded in the tube.

Alternatively, reinforcing means can be around the outer diameter of the external part of the catheter. A plurality of openings are also provided on the anterior side of the distal tube to facilitate mixing of the oxygen with the air being breathed in by the patient. The openings are laterally spaced about a mid-line along the anterior side of the wall of the catheter through an arc of about 120°, i.e., up to about 60° on either side of the midline. A connector is attached to the outwardly extending proximate end of the tube a sufficient distance so as to be capable of being viewed by the patient so that the patient is better able to connect the catheter to a source of oxygen. Stabilizing means are provided so as to enable the patient to reduce the inadvertent movement of the catheter when it is in place and in use. With this arrangement, the proximate portion of the catheter extends out from the patient so that the connector on the proximate end thereof can be viewed by the patient to facilitate his connecting and disconnecting the oxygen supply and to facilitate cleaning the catheter on an outpatient basis, if necessary. The distal end is tapered with the posterior side being longer than the anterior side so as to direct oxygen away from the posterior wall against which it gently rests.

The invention also contemplates a method of inserting a transtracheal catheter in the trachea of a patient. The method comprises, under local anesthesia, the steps of infiltrating the soft tissue overlying the anterior side of the cervical trachea; advancing a hypodermic needle through the anesthesized tissue into the trachea; injecting local anesthetic into the trachea through the needle; inserting a guide wire through the needle; removing the needle over the guide wire; inserting a tissue dilator over the guide wire to enlarge the tract; removing the dilator; inserting a stent over the guide wire and through the enlarged tract; removing the guide wire; securing the stent by appropriate means, in place for a first period of time while initial healing of the dilated tract occurs so as to allow air to freely pass out through the lumen of the stent during coughing, rather than accumulating under the skin with the adherent risk of injury; removing the stent; inserting a temporary catheter in the tract; securing the temporary catheter in place for a second longer period of time until the tract completely matures; removing the temporary catheter; inserting a removable final catheter and releasably securing the final catheter in place. This unique method allows the use of a small needle for the insertion of a catheter which is larger than the needle, and capable of providing sufficient supplemental oxygen for oxygen therapy with active patients but not so large as to require an operation to insert.

The preferred apparatus for carrying out the foregoing method can be provided in the form of a first kit. The transtracheal catheter described hereinbefore is one piece of the apparatus contained in the second kit. The first kit preferably includes a hypodermic needle for forming the small tract or fistula through the trachea and for use with a syringe for injecting an anesthetic into the trachea after the needle is inserted through the trachea to form the tract. The first kit also includes a guide wire for insertion through the needle to maintain the tract after the needle is removed. The guide wire is marked at 11 cm. to prevent over-inserting. A dilator is also provided, which is tapered and has a central passageway for threading it over the guide wire so that it can be used to gradually stretch the tissue to increase the diameter of the tract or opening. The dilator is marked at 7 cm. to prevent over insertion. The dilator is then removed while keeping the guide wire in place. A stent, having a central passageway is also provided in the kit and is inserted in the dilated tract after the dilator is removed in order to maintain the size of the tract or opening to facilitate initial healing of the tract. The guide wire is then removed. The stent is held in position during healing by suturing.

The second kit includes a catheter which has a single opening at a beveled distal end and replaces the stent. The beveled end on the temporary catheter is longer on the posterior or superior side so that the oxygen stream is directed away from the mucosa and toward the center of the trachea. The temporary catheter can be connected to a supply of oxygen during this period and remains in place until healing is complete. A cleaning rod is also included in the second kit which is used periodically to clean out mucous plugs which may form in the distal end of the temporary catheter. To facilitate disconnecting and reconnecting the oxygen supply and the cleaning of the catheter, the proximate end of the catheter extends a sufficient distance outwardly from the surface of the neck and the stabilizing flange on the catheter so that the patient can see the connector thereon over his chin. Finally, the third kit includes a removable, final catheter which has the same dimensions as the temporary catheter and replaces the temporary catheter at the end of the tract healing period. The final catheter has a tapered distal end like the temporary catheter and also has a series of spaced openings in the anterior side wall thereof to facilitate mixing of the oxygen supplied through the tube with the air inhaled by the patient. These openings are spaced about an arc which does not exceed 60° from the midline on the anterior side of the tube.

The kits which have been described, together with the unique temporary and final catheters, provide the means for installing the catheters by a unique method. The catheters are suitable for outpatient use over extended periods of time by patients suffering from COPD. The catheters can be cleaned by the patients, the final catheter being removable by the patient for cleaning and reinsertion. Because of the external extension of the proximate end of the tube beyond the connecting flange of the disclosed fastening means, the patient can see the connector and easily manipulate it to connect and disconnect the oxygen.

Additional advantages of the invention will become apparent from the description which follows, taken in conjunction with the accompanying drawings.

BRIEF DESCRIPTION OF THE DRAWINGS

FIG. 10 is a side elevation of guide wire which forms a part of a first kit of this invention;

FIG. 11 is a side elevation of the dilator, which forms a part of the first kit of this invention, for use in the method of implanting the transtracheal catheter of this invention;

FIG. 12 is an end view of the distal end of the dilator of FIG. 11;

FIG. 13 is a side elevation of a stent which forms a part of the first kit of this invention;

FIG. 14 is a side elevation of a cleaning rod which forms a part of a second kit of this invention;

FIG. 15 is a side elevation of a temporary catheter which forms a part of the second kit of this invention;

FIG. 16 is a side elevation of a removable, final catheter which forms a part of the third kit of this invention;

FIG. 17 is an enlarged vertical section, taken along line 17—17 of FIG. 16, showing the angular spacing of the openings;

FIG. 18 is an enlarged vertical section, taken along line 18—18 of FIG. 16 showing the reinforcing means within the tubing; and FIG. 19 is an enlarged vertical section, taken along line 19—19 of FIG. 16 showing an attachment means for the transtracheal catheter.

FIG. 20 is a graph comparing oxygen therapy by an analysis of blood oxygen during exercise of the catheter of the present invention compared to other therapies.

FIG. 21 is another embodiment of a reinforced catheter useful in the practice of the present invention.

FIG. 22 is a partial sectioned view of the flange utilized with the embodiment shown in FIG. 21.

DETAILED DESCRIPTION OF THE INVENTION

Figure 1:
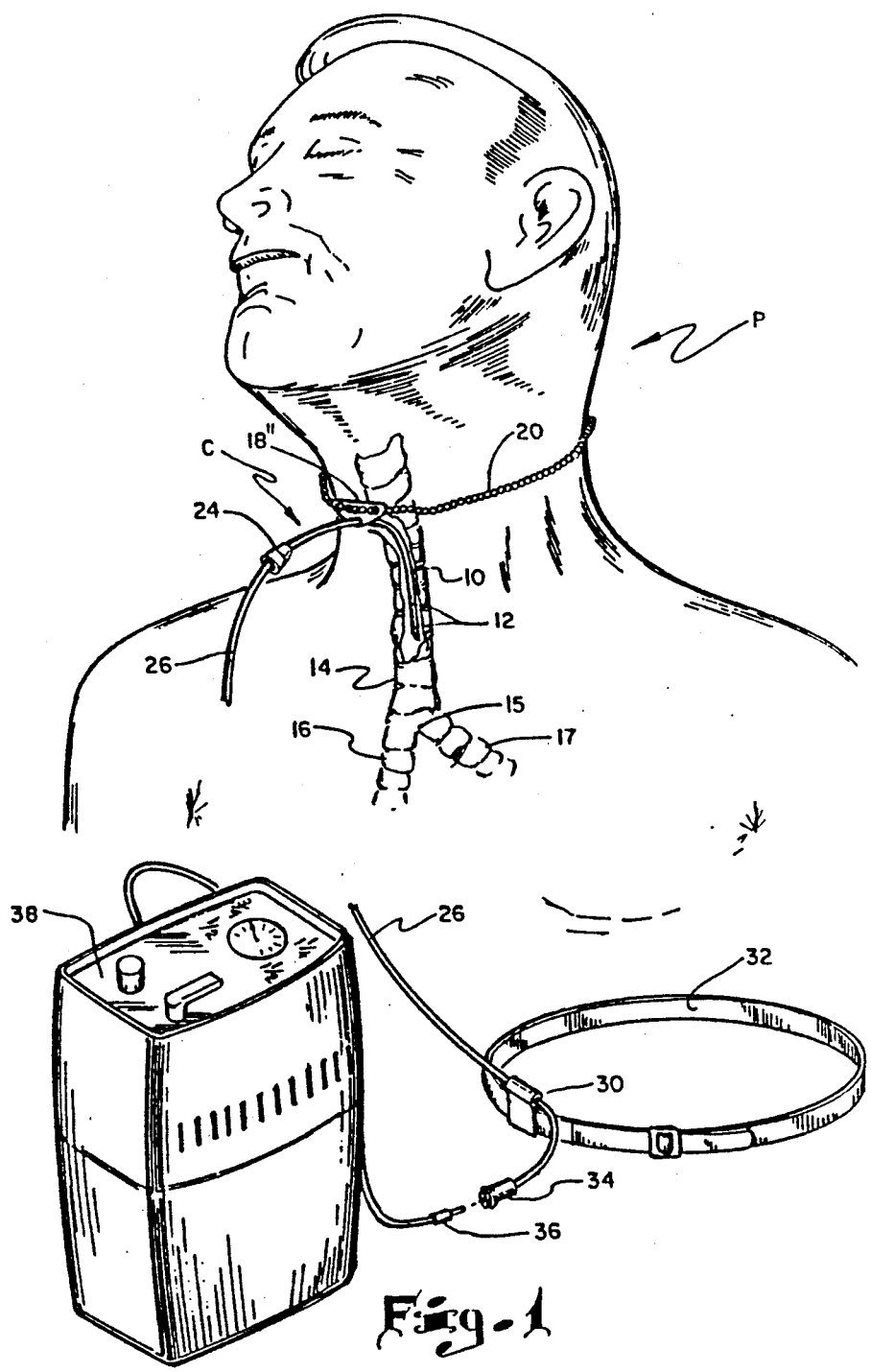
FIG. 1 is a perspective view showing the transtracheal catheter of this invention mounted through the skin and into the trachea of a patient and showing the oxygen supply connecting tube secured to the patient's wearing apparel between the connection to the transtracheal catheter and the connector to a supply of oxygen.

As best seen in FIG. 1, a patient P has been fitted with a transtracheal catheter C. The catheter includes a flexible reinforced tube 10 having a plurality of openings 12 at the distal end thereof. These openings have a specific orientation to facilitate the mixing of the oxygen with the air being breathed by the patient, as more fully explained hereinafter. The distal end, which extends through a tract in the trachea 14, is positioned above the carina 15 to supply the oxygen equally to the right and left bronchus 16 and 17. The catheter is inserted into the cervical trachea, in a manner more fully described hereinafter. After insertion, attachment means 18" is used to secure the catheter C to the patient's neck by means of a chain 20 extending around the patient's neck.

The proximate end of catheter C extends away from the patient's body and has a connector 24 attached to tube 10 through which oxygen is supplied to the patient. Preferably, tube 10 is reinforced, and most preferably, is reinforced by a coil inserted snuggly internally into the lumen. As is readily apparent, the extension provided, makes it possible for the patient to see connector 24 over his chin so as to connect and disconnect the oxygen supply tube and to even remove the catheter, as an outpatient, at home, for cleaning and then replace it and reconnect the oxygen supply. The source of oxygen can be from any source of oxygen such as pressurized oxygen tanks, liquid oxygen reservoirs or oxygen concentrators, with some minor variation in the prescribed flow rates.

As shown in FIG. 1, an intermediate reinforced tube 26 is provided which is connected between connector 24 through clip 30 which is shown on a narrow belt 32 that can be worn underneath the clothes of the patient P. However, the clip 30 can be attached directly to the patient's wearing apparel instead of using a supplemental belt. The connector 34 is then connected to tube 36 to oxygen supply 38. The purpose of this structure is to assure that as the patient moves about the patient will not move to the limit of the tubing and place a stress on catheter C which could pull the catheter out of the trachea and perhaps cause injury or discomfort to the patient. With the intermediate tubing arrangement as shown, any tension would be placed on tube 36 and not on tube 26. In addition, the connector 24 is designed to disengage this also when subjected to a 1 to 3 pound pull.

The catheter system of the present invention includes two catheters. The first is referred to herein as a temporary catheter which is used for a limited period of time while the tract or fistula formed through the trachea heals. The second catheter is referred to as the final catheter which is capable of being used by the patient on a long-term basis but can be removed by the patient, at home, for cleaning on a periodic basis. The differences in these catheters will be more fully explained hereinafter. Both catheters are made of the same material and, with some differences, have the same dimensions. In this regard, for an adult patient, the catheter will have a length of approximately 20 cm and be made preferably of polyurethane, or other elastomeric material having a durameter between about 80 and about 90 Shore A and a relatively small outside diameter, e.g., less than 10 French (3.3 millimeters) and preferably approximately between 1.7 and about 3.0 millimeters, such as to occupy only a small portion of the trachea without impeding normal spontaneous breathing of the patient. The attachment means 18" is located near the midpoint of the tube after placement and is approximately 9 cm from connector 24 on the proximate end of the tube and approximately 11 cm from the distal end of the tube when in place in the trachea. For an adult, the preferred diameter is an 8 French catheter. In some instances, it is contemplated that the inside diameter might be as small as 1.7 mm I.D. It is also contemplated that for pediatric patients the diameter might be as small as 1.0 mm I.D. Of course, the length would be correspondingly shorter to prevent the problems previously discussed.

Figure 2:
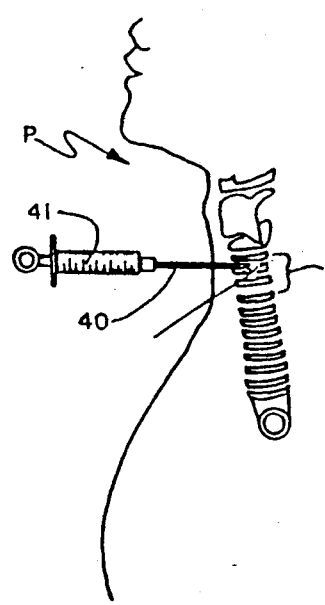
FIG. 2 is a diagrammatical illustration of the infiltration of a local anesthetic into the trachea by means of a needle on a syringe.

The method of inserting transtracheal catheter C is best illustrated in FIGS. 2–7. Conveniently, the method can be carried out by using apparatus contained in three kits. The first kit contains a hypodermic needle, a guide wire, a dilator and a stent. The second kit contains the temporary catheter and a cleaning rod. A final catheter and a cleaning rod are contained in the third kit. In FIG. 2, a local anesthetic is injected into the soft tissues overlying the cervical trachea by means of a hypodermic needle 40 attached to a syringe 41 containing the anesthetic. Typically, a 5 cc syringe is filled with 1% lidocaine and epinephrine at a strength of 1:100,000. The needle may be 27 gauge × 1.25 inches.

Figure 3:
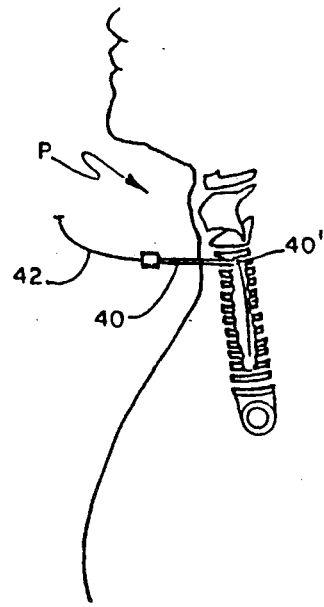
FIG. 3 is a diagrammatical illustration of the insertion of a guide wire through the needle after the syringe is removed.
Figure 4:
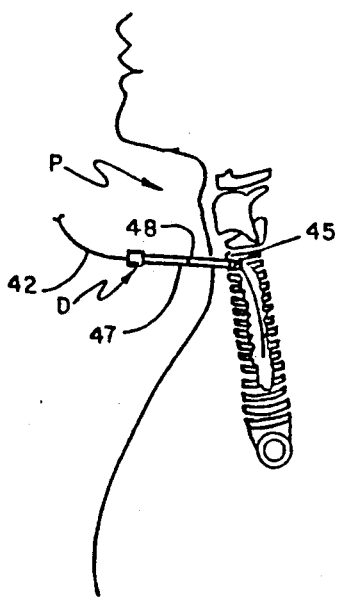
FIG. 4 is a diagrammatical illustration of the insertion of a tissue dilator over the guide wire after the needle is removed.

After local anesthesia is achieved in the skin, a No. 15 scalpel is used to nick the dermis. An 18 gauge thin wall needle, which is in the first kit, is attached to the syringe with the remainder of the anesthetic solution, and the needle is advanced into the trachea. Proper position may be documented by drawing back on the syringe and getting a return of air bubbles in the syringe. The remainder of the anesthetic is then deposited in the trachea. Because of the small size of the needle, the possibility of hemorrhaging is greatly reduced even though the tissue being penetrated is vascular. A 32 cm straight guide wire 42 is passed through the 18 cm gauge thin wall needle 40 into the trachea as seen in FIG. 3. The bevel on the needle and angle of insertion are exploited to direct the guide wire downwardly into the trachea. Conveniently, indicia, such as a notch is provided on the hub of the needle to indicate the orientation of the bevel. The needle 40 is then removed over the guide wire.

As best seen in FIG. 10, guide wire 42 has an atraumatic end 43 which is designed not to scratch or otherwise injure the mucosa or trachea when the wire is inserted. This atraumatic end is preferably about 5 cm long. The wire includes a central longitudinal wire forming a core and a spirally wound wire around the core wire which core wire extends beyond one end of the spiral windings so as to form the flexible atraumatic end. The guide wire has a reference mark, as previously described at about 11 cm from the atraumatic end to help the physician determine the proper depth of insertion.

Next, preferably a 10 French by 15 cm long Teflon dilator D as illustrated in FIG. 11, found in the first kit, having a central bore 46 in the body 47 is passed over the guide wire 42 into the trachea. The dilator has a reference mark 48 inscribed on body 47 at about 7 centimeters to prevent over insertion of the dilator. The initial small tract or fistula created by the hypodermic needle 40 is generally enlarged by the insertion of the taper of distal end 45 of the dilator into the tract. As the dilator is inserted safely by the physician to the mark 48, previously described, see FIG. 11, the tract is stretched without cutting until it is enlarged slightly. The tapered end 45 is preferably about 12 mm long. The dilator remains in place for at about one minute to accomplish sufficient stretching of the tissue.

Figure 5:
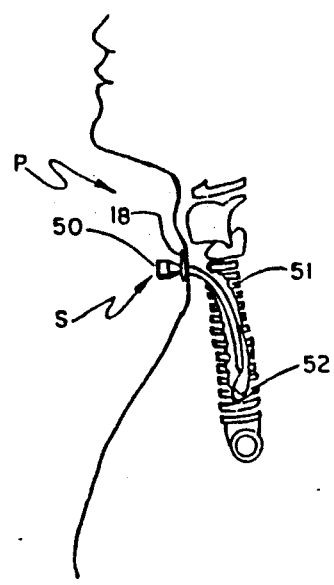
FIG. 5 is a diagrammatical illustration of the insertion of the stent over the guide wire after removal of the dilator.

Next the dilator is removed and the stent S, the final element of the first kit, is passed over the guide wire 42 and through the tract into the trachea, as best seen in FIG. 5. The structure of stent S, with attached flange 18 is illustrated in FIGS. 13.

The flange 18 serves to stabilize the stent by sutures placed through its eyelets and adapts to Luer taper connectors for instillation of lidocaine to suppress coughing. The stent has a body 51 which is made of sufficiently rigid material to hold the tract which has been formed in the trachea open. This stent body 51 has, preferably, a 9 French diameter and is preferably about 11 cm long from the distal tapered end 52 to the proximal end 50. The tapered end 52 facilitates insertion of stent S through the tract in the trachea. A passageway 53 extends through the stent and is maintained open to allow air to pass out of the patient and prevent collection under the skin to minimize the danger of the patient experiencing subcutaneous emphysema, during the process.

Figures 6, 7:
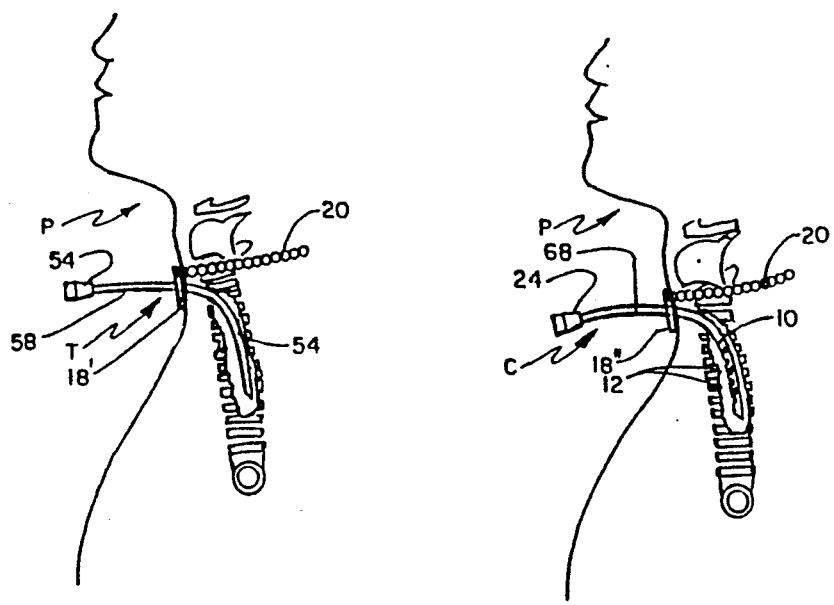
FIG. 6 is a diagrammatical illustration of the insertion of a temporary transtracheal catheter after removal of the stent.
FIG. 7 is a diagrammatical illustration of the insertion of the final catheter, after removal of the temporary catheter.

After typically one week, or longer if indicated, stent S is removed by the physician and a temporary catheter T is inserted, as shown in FIG. 6. The structure of this catheter is best seen by reference to FIG. 16. The temporary catheter is longer than the stent, being about 20 cm in length. In fact, the length of the distal end 54 temporary catheter T which rests inside the trachea is approximately 11 cm long, which is the same length as the distal end of the stent. The temporary catheter has a connector 56 at the proximate end 58 thereof for attachment to an oxygen supply. The extra length of tubing provided by proximate end 58 makes it possible for the patient to see connector 56 so that he can easily connect or disconnect the oxygen supply and can clean the catheter, as described below. This catheter also has a longitudinal passageway 60 extending its entire length and is provided with reinforcing means 61 which may take any form, but is illustrated as being in the form of a helical wire or cord embedded within the tubular material that forms proximate end 58 and distal end 54 of temporary catheter T. The purpose of this armoring is to reduce the possibility of the catheter collapsing, or kinking from any manipulation done by the patient to thereby help assure a constant supply of oxygen to the patient by keeping a constant cross-sectional area in the catheter lumen. This is important since this device will be used by an outpatient who will not be under constant medical supervision. The embodiment shown in FIGS. 21 and 22 illustrate another structure for reinforcing predetermined portions of the catheter against kinking or collapsing during use. The flange 98 (which is shaped and structured as flanges 18, 18' and 18") is provided with a shoulder portion 90 which is shaped to receive a coil reinforcing means 91 (shown in phantom in FIG. 22), which snuggly surrounds the outside of the tube 95, to provide kink and collapse resistance to the tube 95 during use.

Referring again to FIG. 21, the preferred extent of placement of the external reinforcing means 91 to provide the desired reinforcement for the catheter tube 95, is shown. It is contemplated that up to about three inches of coil reinforcement will be sufficient for this application. The coil reinforcement can be made of plastic or metal with adjustment of the size of the reinforcing material to accomplish the desired function.

The distal end of lower portion 54 is tapered to be longer on the posterior side to facilitate insertion and also to deflect the oxygen introduced through the catheter away from the mucosa at the back of the trachea and to direct the oxygen downwardly and slightly forwardly. After proper positioning the temporary catheter T is connected to a source of oxygen. The oxygen flow is then adjusted to achieve a blood oxygen saturation of at least 90% by ear oximetry or arterial blood gas analysis.

Since oxygen is now being supplied to the patient through temporary catheter T, it is necessary to keep passageway or lumen 60 open. This is accomplished by use of a cleaning rod, such as cleaning rod R of FIG. 14. The cleaning rod is conveniently made of a flexible plastic and includes a long shaft 64 which terminates at its upper end in a handle 66 formed as a right angle extension from the shaft 64. Shaft 64 is slightly longer than the total length of the temporary catheter T. To clean out the catheter, the oxygen is disconnected and the shaft 64 of cleaning rod R is inserted through connector 56 and along passageway 60. Because of the sizing, the length of shaft 64 is sufficient to completely expel any mucous which has accumulated within the passageway. Also, the diameter of shaft 64 is just slightly less than the inside diameter of passageway 58. This cleaning is normally done twice a day, or as often as needed. After cleaning, the cleaning rod R is removed and the connector 56 is reconnected to oxygen supply.

The temporary catheter with flange 18' and reinforced as described, is preferably kept in place for six weeks or longer so that the tract or fistula through the trachea can heal completely. After complete healing has occurred, the physician removes the temporary catheter T and provides the patient with a final catheter C which is inserted and positioned as shown in FIG. 7. This catheter is similar to the temporary catheter T with certain differences, as enumerated below.

The structure of the final transtracheal catheter C, which is a part of the third kit, is shown in FIGS. 16–19. The catheter tube 10 is also reinforced, preferably by means such as a coil spring 72 which is partially shown diagrammatically as embedded in the tubing (see FIG. 18) or as shown in FIGS. 21 and 22. The purpose of this armoring is also intended to reduce the possibility of collapse or kinking of the transtracheal catheter which could restrict the oxygen supply to the patient. Conveniently, coil spring 72 extends a sufficient distance along the length of tube 10 to provide the described features with flange or fastening means 18" located at about 9 cm from the proximate connector 24 and about 11 cm from the distal tip. Each side of the fastening means has an aperture 74 (FIG. 19) for receiving a chain 20, or other holding means. The catheter tube 10 is provided with a longitudinal passageway or lumen 76 and the distal end has a taper 78 with a longer posterior side for directing the oxygen away from the mucosa of the trachea. A plurality of openings 12 are spaced about the anterior side of the catheter through an arc of approximately 120° and are all positioned on the portion of the sidewall which faces inwardly from the back wall of the trachea and are located above the shorter end of bevel 78'. In other words, the openings are spaced within 60° to either side of a midline 80 on the anterior side of the tube 10, as shown in FIG. 17.

Figures 8, 9:
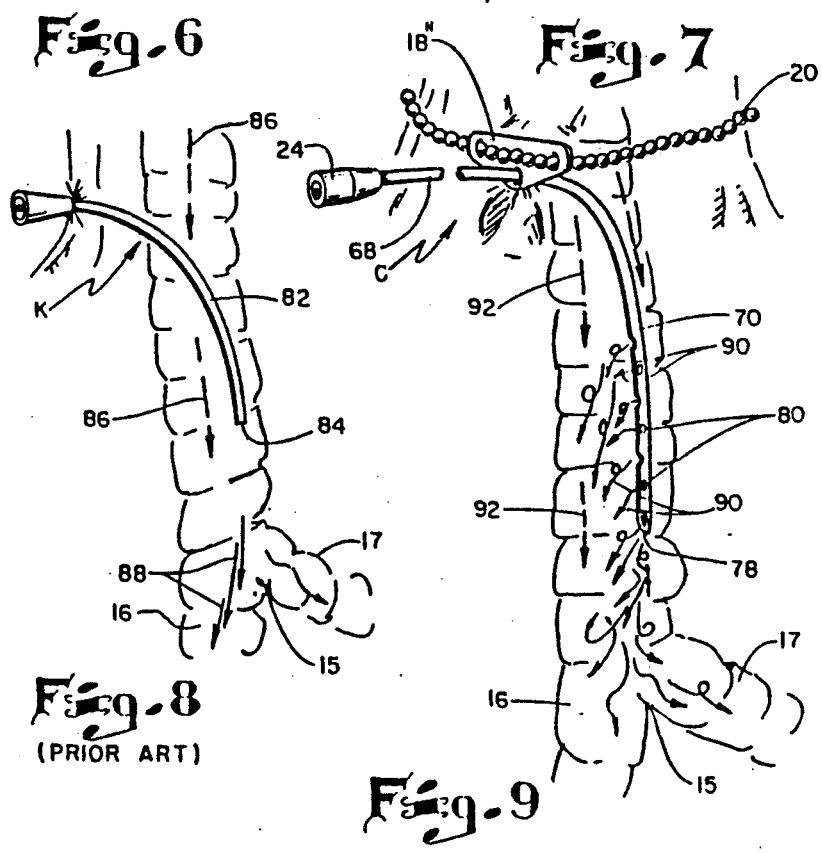
FIG. 8 is a diagrammatic view of the trachea with a flush-mounted prior art catheter showing the orientation of the catheter and the flow of oxygen to the patient from the catheter.
FIG. 9 is a diagrammatic view of the trachea, similar to FIG. 8, but showing the thorough mixing of oxygen and air by means of the catheter of this invention.

The distinct advantage of this arrangement will be apparent from a viewing of FIGS. 8 and 9. In FIG. 8, a prior art catheter K is shown having a tubular body member 82 with a flat distal end 84 and no openings in the sidewall. As can be seen, most of the oxygen is directed straight downwardly in a stream into the right main stream bronchus 16 since it extends on a more straight downwardly path from the trachea than does the left bronchus 17. As a result, air being drawn into the lungs of the patient by normal breathing, as shown by arrows 86, will be less likely to effectively mix with the stream of oxygen from the distal end 84 of catheter K as shown by arrows 88.

On the other hand, in applicant's preferred embodiment, shown in FIG. 9, oxygen is discharged from catheter C through the beveled or tapered distal end 78 and openings 12 so as to be directed away from the mucosa at the back wall of the trachea and out into the body of the trachea as illustrated by arrows 90 to promote better mixing with the air from the patient's natural breathing, as indicated by arrows 92. This will occur because the oxygen is issued in multidirectional streams so that a substantial equal amount of oxygen enriched air passes essentially uniformly into both the right bronchus 16 and the left bronchus 17 and minimizes the drying effect of oxygen on the mucous membranes.

Another important distinction between the prior art catheter K and catheter C is that the connector of catheter K is flush against the trachea whereas the proximate end or extension 68 of catheter C extends outwardly for about 9 cm. This makes catheter C suitable for outpatient use, whereas catheter K is not. With extension 68, the patient can see connector 24 over his chin so that he can connect and disconnect the oxygen supply easily and can periodically remove the catheter for cleaning.

Oxygen is delivered at very low pressures, such as below .2 psi and at low flow rates, which are usually 50% or less than that which is required with a cannula. Of course, the catheter is only for use by a spontaneously breathing outpatient. Individuals who require more than 3 liters per minute by transtracheal catheter either at rest or during exercise can receive up to 6-8 l/min. with the catheter of the present inventions. It can be seen from this chart that with the same flow rates in liters per minute for the 16 gauge catheter and the catheter of the present invention, blood oxygenation is improved for the described device. The nasal cannulae is clearly not as effective as the transtracheal catheters of the present invention even if operated at higher flow rates. Thus, a substantial savings can be obtained from reduced oxygen use while providing active patients with better blood gas values during the therapy. Used on a long-term basis, this difference in efficiency should produce even more advantages to the patient in both the quality of life and extension of useful life.

From the foregoing, the advantages of this invention are readily apparent. A transtracheal catheter has been provided which is safe and comfortable for a spontaneously breathing patient and can be installed in a doctor's office on an outpatient basis without requiring hospitalization. A method of installation is provided whereby the transtracheal catheter may be inserted under a local anesthetic, with the patient remaining ambulatory. Because of its small size, insertion can be accomplished with no risk of severing an artery. The transtracheal catheter is armored so that the possibility of kinking and crushing is minimized to assure a continuous supply of oxygen to the patient. Furthermore, it is convenient for the device to be removed by the patient for cleaning and reinsertion. Disconnection and reconnection of the oxygen supply is facilitated by the extension of the external end. The constant flow of low pressure oxygen into the collapsed airways of emphysema patients helps hold the bronchial tubes open to improve the function of the lungs and reduce the work of breathing.

The above-described method is accomplished by the use of devices which are provided in a first, second and third kits. The first kit includes a needle for forming the initial tract in the trachea; an atraumatic guide wire which is fed through the needle to maintain the tract after the needle is removed; a dilator, which is passed over the guide wire and used to enlarge the tract; and a stent to replace the dilator. A second kit is provided which includes a temporary catheter which replaces the stent and remains in place for a period of several weeks while healing of the tract is completed; a cleaning rod for cleaning the temporary catheter; the third kit includes a removable, final catheter which replaces the temporary catheter after the healing is complete and a cleaning rod.

An important feature of this method is that it allows a small catheter to be inserted by using an even smaller needle to form a tract which is subsequently dilated. The prior art, on the other hand, requires either a large needle for a smaller catheter or a large tract for a large tracheotomy tube to resuscitate a non-breathing patient.

The first kit is an Insertion Tray that provides all the supplies less sterile gloves and facial tissue necessary to create a tract for the transtracheal catheters of the present invention. The paper drape around the tray may be opened to serve as a Mayo stand cover. The Insertion Tray has two tiers. The upper preparatory Tier should be used clean and provides the supplies for puncture site selection, local anesthesia and skin preparation. The Lower and second Procedure Tier should be used sterile and provides the supplies to create a catheter tract and stabilize the stenting device.

The upper tier will preferably contain a surgical marking pen; 2-20" lengths of #3 stainless steel bead chain with connectors; disposable wire cutter; 3-alcohol prep pads; 5 cc Luer tip syringe prefilled with 2% lidocaine with epinephrine 1:100,000; 27 ga×1.25" needle; 21 ga×1.5" needle; Hibiclens soap packet; prep well and sponge stick; and 2-4×4" gauze sponges to dry skin.

The lower tier will preferably contain a Steri-Drape (#1010); 2-4×4" gauze sponges; #15 Bard-Parker scalpel blade on disposable plastic handle; 18 gauge×7 cm thinwall needle; 5 cc Luer tip syringe prefilled with 2 cc saline; 32 cm×0.038" straight guide wire marked at 11 cm; 10 French×15 cm tissue dilator marked at 8 cm; Lubafax packet; 9 French stent; Disposable needle holder; Disposable scissor; 3-0 Nylon suture on FS-1 needle; and a H bandage.

The Insertion Tray therefore provides all the supplies less sterile gloves and facial tissue necessary to create a tract for the transtracheal catheters. Most of the items included in the tray are commercially available and are gathered in an orderly sequence for the convenience of the physician.

| MANUFACTURERS OF INSERTION TRAY COMPONENTS | |
|---|---|
| Surgical Marking Pen | Devon Industries<br>Chatsworth, CA 91311 |
| Stainless Steel bead chain | McMaster-Carr<br>Chicago, IL 60680 |
| Scissor to cut bead chain #32048-022 | American Hospital Supply<br>McGaw Park, IL 60085 |
| Alcohol Prep pads | The Kendall Company<br>Hospital Products<br>Boston, MA 02101 |
| 5 cc Luer taper syringe prefilled with 2% Xylocaine with epinephrine 1:100,000 | American Pharmaseal<br>Laboratories<br>Glendale, CA 91209 |
| Monoject 27 ga × 1.25" needle | Sherwood Medical<br>St. Louis, MO 63103 |
| Monoject 21 ga × 1.5" needle | Sherwood Medical<br>St. Louis, MO 63103 |
| Hibiclens Soap | Stuart Pharmaceuticals<br>Wilmington, DE |
| Sponge sticks | Johnson & Johnson<br>New Brunswick, NJ 08903 |
| 4 × 4" gauze sponges | Johnson & Johnson<br>New Brunswick, NJ 08903 |
| Steri-Drape #1010 | Surgical Products<br>Division/3M<br>St. Paul, MN 55144 |
| 4 × 4" gauze sponges | Johnson & Johnson<br>New Brunswick, NJ 08903 |
| #15 Bard-Parker scalpel on disposable handle | Becton Dickinson & CO.<br>Lincoln Park, NJ 07035 |
| 18 ga × 7 cm thin wall needle | Cook Inc.<br>Bloomington, IN 47402 |
| 5 cc Luer taper syringe prefilled with 2 cc saline | American Pharmaseal Labs<br>Glendale, CA 91209 |
| Lubafax packet | Burroughs Wellcome Co.<br>Research Triangle Park |
| Webster needle holder #32042-042 | American Hospital Supply<br>McGaw Park, IL 60085 |
| Suture scissor | American Hospital Supply<br>McGaw Park, IL 60085 |
| 3-0 Nylon suture on FS-1 needle | Ethicon Inc.<br>Somerville, NJ 08876 |
| H-bandage | Johnson & Johnson<br>New Brunswick, NJ 08903 |

The remaining apparatus is constructed as described, with biocompatible materials where necessary. For example, the temporary and permanent catheters are preferably constructed as described from medical grade polyurethane which is coated with a hydrophilic polymer in the areas which are exposed to tracheal secretions. The polymer provides a lubricious surface for ease of insertion and removal. The polymer, also minimizes adherence of mucous to the catheter.

The bevel of the tip of temporary and permanent catheters, and the side ports of the permanent catheter direct oxygen away from the tracheal mucosa toward the center of the air column in the trachea. This promotes patient comfort. Proper orientation is facilitated by an asymmetric flange as the fastening means (see FIG. 9). Improper orientation may affect comfort but does not comprise efficacy.

The 9 cm extension of tubing from the flange to the female Luer taper connector removes the bulk of the connectors away from the collar. It also makes manipulation of the connectors easier for the patient. In addition, the 2 pound release (range 1-3 pounds) of the female Luer taper connector is a feature which will result in a safety disconnect rather than catheter dislodgement in the event of an excessive pull on the proximal end of the Oxygen Hose.

The Cleaning Rod is designed to remove debris as it is passed through the lumen of either the temporary or permanent catheter. The length is preferably 5 mm longer than the catheter, and over-insertion or loss down the catheter is prevented by the 2 cm handle which is at a 90° angle and the small cap at the end of the handle.

Both, the temporary and permanent catheters of the present invention have an outside diameter less than the 10 French tissue dialator and are most preferably 8 French reinforced tubes made of medical grade clear polyurethane with nylon coil spring reinforcement and approximately 20 cm (7.875") in length.

The attachment means or security flange is most preferably made of Kraton or polyethylene, and is clear.

Procedure

Candidates for this procedure should demonstrate a need for chronic oxygen therapy by having arterial blood gases analysis of $PaO_2$ of less than 55 Torr and a $SaO_2$ analysis of less than 90% on room air during appropriate medical therapy. The use of transtracheal oxygen offers the patient greater mobility, improved cosmesis, and avoidance of nasal irritation by cannulae. Patients who are inadequately oxygenated with nasal cannulae or 16 gauge transtracheal catheters may benefit from better oxygenation with the catheter of the present invention. The recommended pre-puncture evaluations should identify individuals for whom transtracheal oxygen therapy is contraindicated and others who require special considerations in the course of treatment.

The Puncture Technique uses an 18 gauge needle, wire guide and dilator to stretch an opening into the trachea with minimal discomfort. About one hour before the puncture, the patient is given is given oral prophylactic antibiotic with a sip of water. If not contraindicated, an oral narcotic is also administered for minor sedation and cough suppression. The patient removes his top and puts on a hospital gown. He is seated in a procedure chair with a head rest, and the head is elevated slightly to reproduce the position of the neck while looking in a mirror during catheter changes. Oxygen is continued throughout the procedure, but cannulae are repositioned so that they arrive from behind the head and do not interfere with the anterior neck. The Insertion Tray is removed from its plastic bag and placed on a Mayo stand at chest level in front of the patient. The paper wrapping is opened fully to act as a sterile drape for the Mayo stand. The superficial anatomy of the anterior neck is palpated carefully, and the notch of the thyroid cartilage, the cricothyroid membrane and the notch of the manubrium are marked using the surgical marking pen. Visible anterior jugular veins should also be marked. A #3 stainless steel bead chain necklace is then placed around the patient's neck and trimmed with wire cutters to fit snuggly but still accommodate one finger. The chain is rolled down onto the trapezius muscles, and the intersection of the cervical trachea and necklace is marked for subsequent puncture. The highest acceptable puncture should be the tracheal interspace immediately below the cricoid cartilage (cricotracheal ligament), and the lowest should be the level of the manubrium. Occasionally a less snug necklace will be required to reach a low cricotracheal puncture site. A second length of bead chain is included for occasions when the first is cut too short. The customized chain is removed and placed in a labeled envelope for later use. The skin over the puncture site is prepared with an alcohol swab without removing the orientation marks. The prefilled 5 cc syringe containing 2% lidocaine with epinephrine 1:100,000 is attached to the 27 ga × 1.25" needle. At the selected site, about 2 cc of this solution is infiltrated into the skin about 2 cm on either side of midline, and about 1 cc of local anesthetic is deposited into deeper pretracheal tissues. The needle is then exchanged for a 22 ga × 1.5" needle. Facial tissue is given to the patient who is informed of an incipient cough, bad taste and globus sensation caused by the local anesthetic. The needle is passed transtracheally at the puncture site, and the remainder of local anesthetic quickly deposited onto the tracheal mucosa. A brief paroxysm of coughing may result. The anterior neck is prepared with Hibiclens soap using a sponge stick. Hibiclens soap is preferred to various iodophors because it is nonstaining and better suited for this outpatient procedure. The skin is then blotted dry with gauze so that the procedure drape will stick to the skin. The upper Preparatory Tier is then removed from the Mayo stand to expose the lower Procedure Tier which should remain sterile. Surgical gloves are put on, and the Steri-Drape is applied to the upper chest at the level of the clavicles.

A 1 cm vertical incision centered at the puncture site is made with a #15 scalpel. Gauze sponge is held in the palm of the other hand while transfixing the trachea to maintain orientation. The incision should pass completely through the dermis into fat. Obvious anterior jugular veins should be avoided. The 18 ga needle attached to the syringe containing saline is then directed through the incision down to the trachea. Tracheal cartilages are palpated, and the needle is popped through an interspace. Air is aspirated into the syringe which is then removed. The notch on the hub of the needle is rotated until it is on the lower rim, and the tip of the needle is angled downward 45° toward the carina. The atraumatic end of the wire guide should pass freely into the lower airway up to 11 cm in depth. If it is does not pass easily, the needle should be repositioned. The needle is withdrawn, and the 11 cm mark on the wire guide is positioned at the skin level. The 10 French dilator is then firmly advanced over the wire guide into the trachea but not more than the 8 cm. After one minute of stretching, the dilator is removed and exchanged for the 9 French stent. Insertion of the stent is facilitated by a small amount of water soluble jelly on its tip and constant twirling during gentle advancement. The wire guide is then removed.

The disposable needle holder and scissor are used to suture the stent to the skin with 3-0 nylon suture. Sutures can be placed through each of 2 eyelets on a flange of the stent taking care not to close the midline incision. The skin and lumen of the stent should remain open to minimize the risk of subcutaneous emphysema. The H-bandage is then applied taking similar care not to create an occlusive dressing.

The patient is sent to the radiology department for posteroanterior and lateral chest xrays to document catheter position and absence of pneumothorax and subcutaneous emphysema. Nasal cannulae oxygen is continued during the stent week, and oxygen should not be administered through the stent. Significant bleeding has not been observed because the method is relatively atraumatic. Because the stent functions as a drain, bacterial infection of the tract has not been observed.

After one week of stenting, the temporary transtracheal catheter is inserted by the physician over a wire guide, and transtracheal oxygen therapy is begun. The temporary catheter is designed to remain in place during the early weeks of transtracheal oxygen therapy when the tract is maturing. After the tract has sufficiently healed, usually six weeks, the final catheter is inserted in the tract. The final catheter can be removed by the patient for cleaning as well as be cleaned in place. The temporary and final catheters can be cleaned in place using the Cleaning Rod and sterile saline. The kink and crush resistant Oxygen Hose adapts standard oxygen sources to the catheter. Inadvertent decannulation is protected against by the suspender-type security clip which attaches to the top of the pants belt or dress and the 2 pound safety release of the Luer taper connector between the hose and the catheter.

In summary, the durometer values, i.e. about 80–90, Shore A selected for the final configurations of the temporary and permanent catheters of the present invention are desirable and indeed necessary for proper insertion and long-term patient comfort. In this regard, the spacing for the location of the holes of the distal end of the permanent catheter are preselected, within the range of orientation described, to retain a sufficient flexibility and stiffness to facilitate proper insertion, removal and cleaning, as well as enabling proper orientation, when in place, in order to achieve the benefits described herein. The 8 French size of the temporary and permanent catheters is the most preferred size since tests have shown that it is the smallest diameter compatible with back pressure limits, for a preselected range of oxygen flow rates.

It is contemplated that the inventive concepts herein described may be variously otherwise embodied and it is intended that the appended claims be construed to include alternative embodiments of the invention except insofar as limited by the prior art.

What is claimed is:

1. An apparatus for supplying oxygen to supplement the ventilation of a patient without interfering with the normal breathing of said patient, said apparatus comprising:

a transtracheal catheter for insertion into the trachea of the patient, said transtracheal catheter including:
an elongated flexible tube formed of a biocompatible material having a proximate end and a distal end;
connection means affixed to the proximate end of said tube connecting said tube to an oxygen supply for providing oxygen into said tube; and
said tube including:
an inside diameter between 1.7 and 2.5 millimeters to provide oxygen through said tube with an outside diameter substantially less than the cross-sectional area of the patient's trachea so not to interfere with spontaneous breathing of the patient;
a length sufficient to locate the proximate end of said tube external to the neck of the patient and to locate the distal end of said tube through a surgically formed opening in the trachea of said patient to an area above and adjacent the carina of the patient;
an opening formed in said distal end of said tube to disperse oxygen into the lungs of said patient without interfering with the normal breathing of said patient, and
a tube wall structure and thickness such as to enable flexible insertion of said tube into said trachea of said patient while resisting deformation of said tube.

2. The apparatus of claim 1 wherein said tube wall structure includes a durometer range between 80 to 90 Shore A.

3. The apparatus of claim 1 wherein said transtracheal catheter further includes a hydrophilic coating on at least the outer and inner portions of said tube adjacent said distal end of said tube to limit adhesion and build-up of mucous-type materials present in the trachea of the patient.

4. The apparatus of claim 1 wherein said tube further includes reinforcement means for maintaining a constant lumen cross-section in at least a portion of said tube.

5. The apparatus of claim 1 wherein said catheter further comprises locating abutment means affixed to said tube near said proximate end of said tube for locating said tube relative to the surgically formed opening in said patient and in abutting engagement with the neck of said patient.

6. The apparatus of claim 1 wherein said opening in said distal end of the tube includes an elliptical end opening facing forwardly toward the front of said trachea to direct the oxygen flowing out of said tube toward the front of the trachea.

7. The apparatus of claim 6 wherein said opening in said distal end of said tube further includes a plurality of side openings located at approximately between 30 to 60 degrees on either side of said end opening to direct said flow of oxygen toward the front of the trachea.

8. An apparatus for supplying oxygen to supplement the ventilation of a patient without interfering with the normal breathing of said patient, said apparatus comprising:
    a transtracheal catheter for insertion into the trachea of the patient, said transtracheal catheter including:
        an elongated flexible tube formed of a biocompatible material having a proximate end and a distal end;
        connection means affixed to the proximate end of said tube connecting said tube to an oxygen supply for providing oxygen into said tube; and
        said tube including:
        an outside diameter in the range of 2.1 millimeters and 3.0 millimeters to be substantially less than the cross-sectional area of the patient's trachea so not to interfere with spontaneous breathing of the patient;
        a length sufficient to locate the proximate end of said tube external to the neck of the patient and to locate the distal end of said tube through a surgically formed opening in the trachea of said patient to an area above and adjacent the carina of the patient;
        an opening formed in said distal end of said tube to disperse oxygen into the lungs of said patient without interfering with the normal breathing of said patient, and
        a tube wall structure and thickness such as to enable flexible insertion of said tube into said trachea of said patient while resisting deformation of said tube.

9. The apparatus of claim 8 wherein said transtracheal catheter further includes a hydrophilic coating on at least the outer and inner portions of said tube adjacent said distal end of said tube to limit adhesion and build-up of mucous-type materials present in the trachea of the patient.

10. The apparatus of claim 8 wherein said tube further includes reinforcement means for maintaining a constant lumen cross-section in at least a portion of said tube.

11. The apparatus of claim 8 wherein said catheter further comprises locating abutment means affixed to said tube near said proximate end of said tube for locating said tube relative to the surgically formed opening in patient and in abutting engagement with the neck of patient.

12. The apparatus of claim 8 wherein said opening in said distal end of said tube includes an elliptical end opening facing forwardly toward the front of the trachea to direct the oxygen flowing out of the tube toward the front of said trachea.

13. The apparatus of claim 12 wherein said opening in said distal end of said tube further includes a plurality of side openings located at approximately between 30 to 60 degrees on either side of said end opening to direct said flow of oxygen toward the front of the trachea.

14. The apparatus of claim 8 wherein said tube wall structure includes a durometer range between 80 to 90 Shore A.

15. An apparatus for supplying oxygen to supplement the ventilation of a patient without interfering with the normal breathing of said patient, said apparatus comprising:
    a transtracheal catheter for insertion into the trachea of the patient, said transtracheal catheter including:
        an elongated flexible tube formed of a biocompatible material having a proximate end and a distal end;
        connection means affixed to the proximate end of said tube connecting said tube to an oxygen supply for providing oxygen into said tube; and
        said tube including:
        an outside diameter substantially less than the cross-sectional area of the patient's trachea so not to interfere with spontaneous breathing of the patient;
        an inside diameter sufficient to provide oxygen through said tube at flow rates greater than two liters per minute while maintaining a back pressure of less than approximately two psi;
        a length sufficient to locate the proximate end of said tube external to the neck of the patient and to locate the distal end of said tube through a surgically formed opening in the trachea of said patient to an area above and adjacent the carina of the patient;
        an opening formed in said distal end of said tube to disperse oxygen into the lungs of said patient without interfering with the normal breathing of said patient, and
        a tube wall structure and thickness such as to enable flexible insertion of said tube into said trachea of said patient while resisting deformation of said tube.

16. The apparatus of claim 15 wherein said opening in said distal end of said tube includes an elliptical end opening facing forwardly toward the front of the trachea to direct the oxygen flowing out of the tube toward the front of said trachea.

17. The apparatus of claim 16 wherein said opening in said distal end of said tube further includes a plurality of side openings located at approximately between 30 to 60 degrees on either side of said end opening to direct said flow of oxygen toward the front of the trachea.

18. The apparatus of claim 15 wherein said tube wall structure includes a durometer range between 80 to 90 Shore A.

19. The apparatus of claim 15 wherein said apparatus includes a hydrophilic coating on at least the outer and inner portions of said tube adjacent said distal end of said tube to limit adhesion and build-up of mucous-type materials present in the trachea of the patient.

20. The apparatus of claim 15 wherein said apparatus includes reinforcement means for maintaining a constant lumen cross-section in at least a portion of said tube.

21. The apparatus of claim 15 wherein said catheter further comprises locating abutment means affixed to said tube near said proximate end of said tube for locating said tube relative to the surgically formed opening in the patient and in abutting engagement with the neck of the patient.

* * * * *